(12) United States Patent
Yekutiel et al.

(10) Patent No.: US 12,706,220 B2
(45) Date of Patent: Aug. 11, 2026

(54) INPUT AUGMENTATION FOR GUIDING GENERATIVE APPLICATIONS IN EVIDENCE-SUPPORTED CLINICAL INFORMATION EXTRACTION

(71) Applicant: Microsoft Technology Licensing, LLC, Redmond, WA (US)

(72) Inventors: Shahar Yekutiel, Tel Aviv (IL); Ksenya Kveler, Nesher (IL); Rachel Wities, Givat Shmuel (IL); Aaron Toby Bornstein, Zikhron Ya'akov (IL); Tom Timianker, Tel Aviv (IL); Ran Efrati, Tel-Aviv (IL); Yahav Amsalem, Tel-Aviv (IL); Hadas Bitran, Ramat-HaSharon (IL); Uri Einav, Herzelia (IL)

(73) Assignee: Microsoft Technology Licensing, LLC., Redmond, WA (US)

( * ) Notice: Subject to any disclaimer, the term of this patent is extended or adjusted under 35 U.S.C. 154(b) by 0 days.

(21) Appl. No.: 18/904,053

(22) Filed: Oct. 1, 2024

(65) Prior Publication Data

US 2026/0094726 A1 Apr. 2, 2026

(51) Int. Cl.
*G16H 50/70* (2018.01)
*G06F 16/334* (2025.01)
(Continued)

(52) U.S. Cl.
CPC ........... *G16H 50/70* (2018.01); *G06F 16/334* (2019.01); *G06F 16/338* (2019.01); *G06F 40/117* (2020.01); *G06F 40/295* (2020.01)

(58) Field of Classification Search
CPC ..................................................... G16H 50/70
See application file for complete search history.

(56) References Cited

U.S. PATENT DOCUMENTS

2018/0068076 A1* 3/2018 Farri ..................... G16H 70/60
2020/0218719 A1* 7/2020 Eifert ..................... G06F 16/35
(Continued)

OTHER PUBLICATIONS

"Sequential Organ Failure Assessment (SOFA) Score", Predicts ICU mortality based on lab results and clinical data, Retrieved from URL: https://www.mdcalc.com/calc/691/sequential-organ-failure-assessment-sofa-score, Retrieved Date Jul. 9, 2025, 4 Pages.

*Primary Examiner* — Van H Oberly
(74) *Attorney, Agent, or Firm* — Barta Jones, PLLC

(57) ABSTRACT

Example solutions for augmenting text inputs for analyzing clinical documents include: identifying a clinical named entity within text content of a clinical input document; adding an anchor tag to the text content, the anchor tag including an entity ID and a clinical attribute associated with the clinical named entity, thereby generating an enhanced input document; and submitting a first query prompt and the enhanced input document to a generative artificial intelligence (GAI) model, the first query prompt including task text and anchoring markup text, the task text includes instructions of a task to be performed by the GAI model on the enhanced input document, the anchoring markup text includes a template of the anchor tag and instruction to add a reference anchor tag to output generated by the GAI model, where the reference anchor tag is to include the entity ID and the clinical attribute of the anchor tag.

20 Claims, 6 Drawing Sheets

(51) Int. Cl.

| | |
|---|---|
| ***G06F 16/338*** | (2019.01) |
| ***G06F 40/117*** | (2020.01) |
| ***G06F 40/295*** | (2020.01) |

(56) References Cited

U.S. PATENT DOCUMENTS

| | | | | |
|---|---|---|---|---|
| 2024/0013000 | A1* | 1/2024 | Li | G06F 40/40 |
| 2025/0200208 | A1* | 6/2025 | Roper, Jr. | G06F 21/6218 |

* cited by examiner

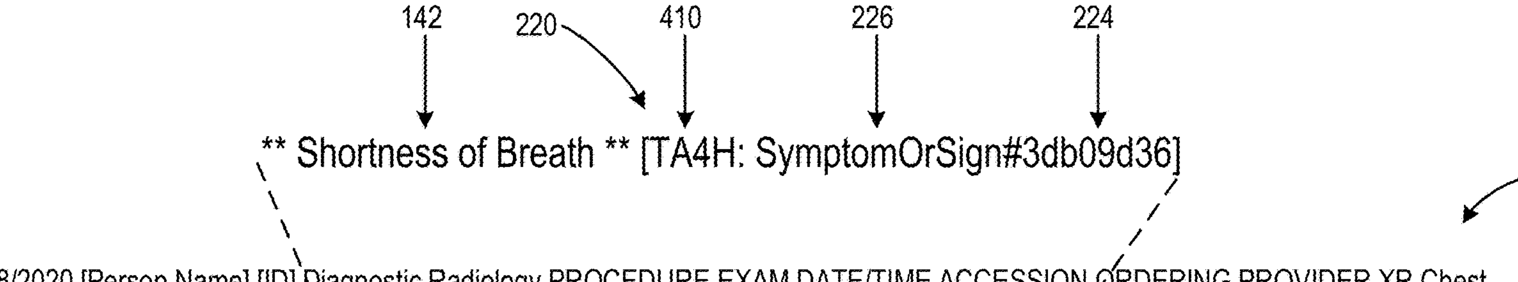

Admit Date: 9/28/2020 [Person Name] [ID] Diagnostic Radiology PROCEDURE EXAM DATE/TIME ACCESSION ORDERING PROVIDER XR Chest 1 View Bedside 9/28/2020 12:48 MDT XR-20-0034229 [Person Name] MD Reason for Exam (XR Chest 1 View Bedside) Shortness of Breath [TA4H: SymptomOrSign#3db09d36]

Report Technique: Single frontal portable view of chest. COMPARISON: 20 September 2020. INDICATION: Shortness of breath [TA4H: SymptomOrSign#269c252a]. NSCLC [TA4H: Diagnosis#ecda9110]. FINDINGS: Right-side chest port is stable [TA4H: SymptomOrSign#46fa8a75]. There is scarring [TA4H: SymptomOrSign#a8c4be52] within the right mid upper lung.

There is increased interstitial airspace opacities [TA4H: SymptomOrSign#91f9596e] within the left lower lung. Cardiac silhouette is mildly enlarged [TA4H: SymptomOrSign#68bad26c], unchanged.

Osseous structures are intact [TA4H: SymptomOrSign#5defb3d]. IMPRESSION: Increased interstitial airspace opacities [TA4H: SymptomOrSign#68bad26c], unchanged.

Osseous structures are intact [TA4H: SymptomOrSign#5d7efb3d]. IMPRESSION: Increased interstitial airspace opacities [TA4H: SymptomOrSign#3aac3aed] within the left lower lung, findings suggestive of pneumonia [TA4H: Diagnosis#b492b55c]. Exam was reported by [Person Name], [ID], on 9/28/2020 12:59 *** Final *** Signed by: [Person Name] MD Signed (Electronic Signature): 9/28/2020 1:04 pm Reported by: [Person Name]

FIG. 4

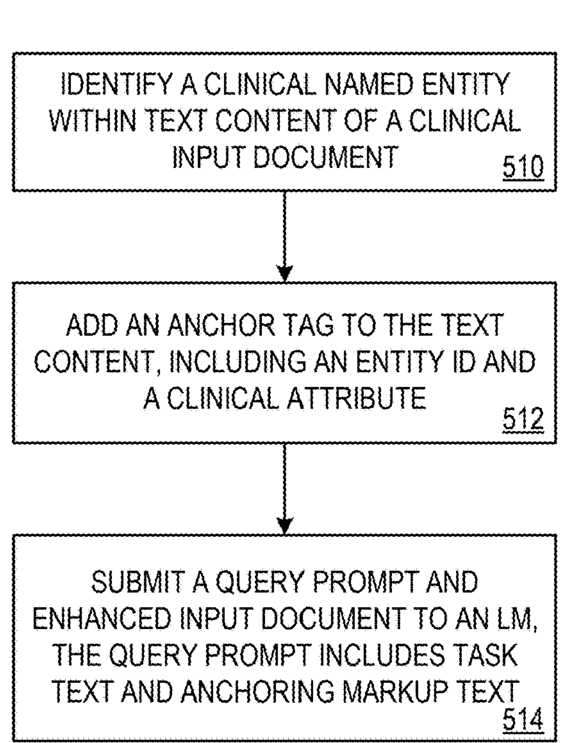
FIG. 5

INPUT AUGMENTATION FOR GUIDING GENERATIVE APPLICATIONS IN EVIDENCE-SUPPORTED CLINICAL INFORMATION EXTRACTION

BACKGROUND

In the field of information extraction in unstructured clinical documents (e.g., admission notes, discharge summaries, radiology narratives, and the like), generative artificial intelligence (GAI) models such as large language models (LLMs) can be leveraged to analyze documents to, for example, generate summarizations, automate form filling, perform statistical analysis, assist in decision support, and more. However, due to domain sensitivity and potential impact on health outcomes, accuracy in output is of paramount importance.

SUMMARY

The disclosed examples are described in detail below with reference to the accompanying drawing figures listed below. The following summary is provided to illustrate some examples disclosed herein. The following is not meant, however, to limit all examples to any particular configuration or sequence of operations. Example solutions for augmenting text inputs for analyzing clinical documents include: identifying a clinical named entity within text content of a clinical input document; adding an anchor tag to the text content, the anchor tag including an entity ID and a clinical attribute associated with the clinical named entity, thereby generating an enhanced input document; and submitting a first query prompt and the enhanced input document to a generative artificial intelligence (GAI) model, the first query prompt including task text and anchoring markup text, the task text includes instructions of a task to be performed by the GAI model on the enhanced input document, the anchoring markup text includes a template of the anchor tag and instruction to add a reference anchor tag to output generated by the GAI model, where the reference anchor tag is to include the entity ID and the clinical attribute of the anchor tag.

BRIEF DESCRIPTION OF THE DRAWINGS

The disclosed examples are described in detail below with reference to the accompanying drawing figures listed below:

FIG. 4 illustrates example text of enhanced input document after anchor tags have been added to the example input document shown in FIG. 3;

FIG. 5 is a flowchart illustrating exemplary operations performed by the system of FIG. 1 for identifying clusters within source data.

Corresponding reference characters indicate corresponding parts throughout the drawings. Any of the drawings may be combined into a single example or embodiment.

DETAILED DESCRIPTION

Figure 1:
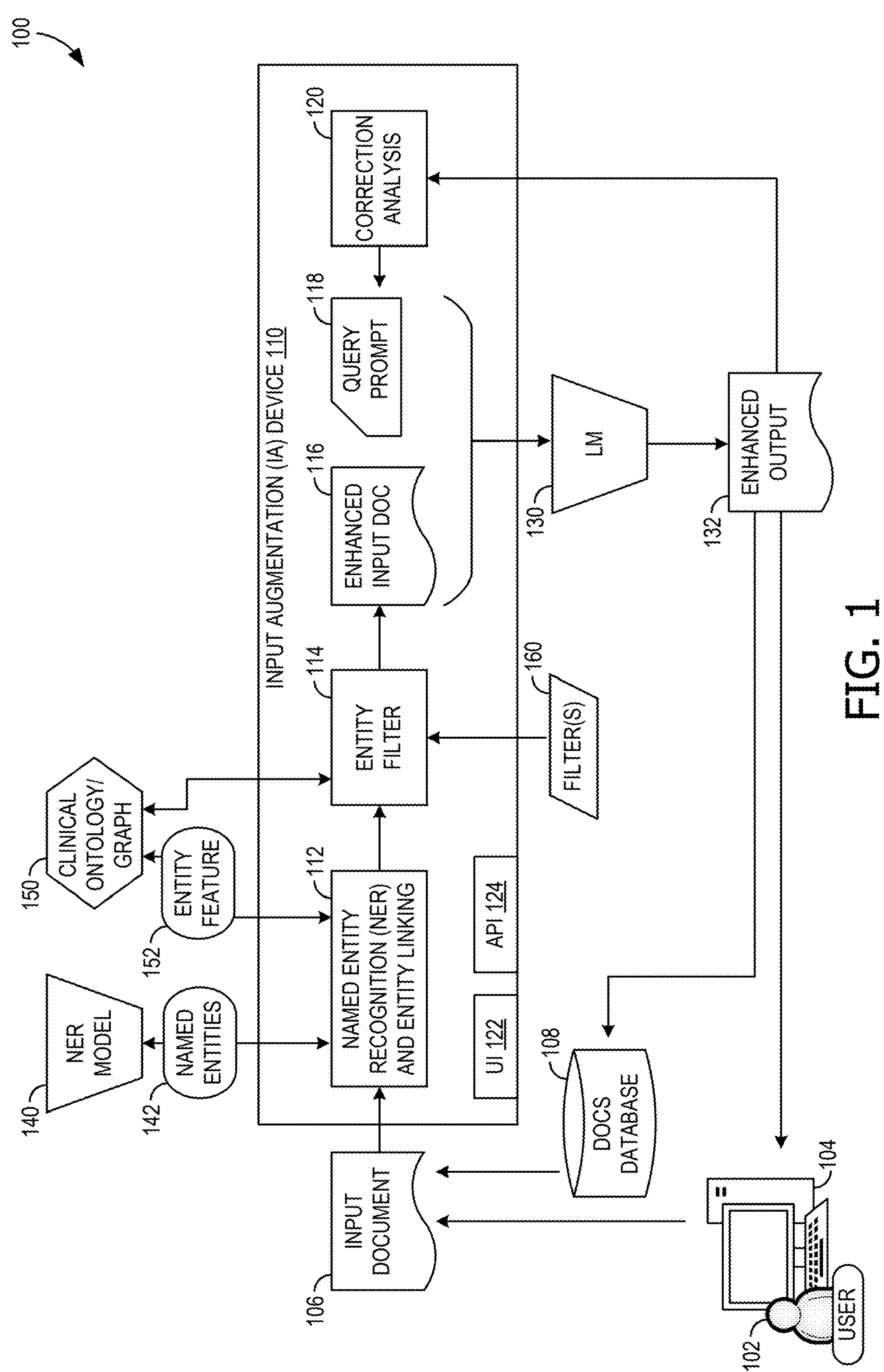
FIG. 1 illustrates an example architecture of an input augmentation (IA) system in which an IA device performs various analytics tasks on clinical documents using a generative AI model, such as LM.

Existing attempts to leverage language models (LMs) in analyzing clinical documents have resulted in several major issues. One notable problem is that information extraction can have errors or low quality. For example, "noise" is often present in LM output, leading to inadequate focus, imprecision, and irrelevance within the output (e.g., extracted information should precisely reflect the medications, dates, dosages, and examination values mentioned in the original document). Further, some LM output results can lose track of relevant clinical information in the original document, leading to a "lost in the middle" effect, particularly when the original document is long. In some instances, typographic errors, rare abbreviations, or rare conditions can be misunderstood by the LM. In some instances, the output of the LM may be distracted or unfocused on certain types of clinical events, and thus may generate unneeded data in lieu of what is desired by the practitioner. Another problem with applying LMs to such tasks is identifying support in the original document for assertions appearing in the output (a problem referred to herein as the "track-back problem"). Existing solutions are not able to adequately provide evidence from the original document for the various assertions provided in the output.

Some conventional systems attempt to solve these technical problems with prompt engineering approaches (e.g., generating an extensive prompt to help generate better output), post-processing tasks (e.g., analyzing the output and attempting to improve on the output after generation), or retrieval-augmented generation (RAG) (e.g., identifying and adding some additional supporting documents to the prompt, thereby providing additional context to the core query). However, such conventional systems are not able to sufficiently address at least the above-mentioned problems. For example, prompt engineering solutions are typically time consuming for users, often generate unexpected results, and do not solve the track-back problem. Conventional post-processing techniques do not affect the LM output, but attempt to mitigate errors in retrospect if the output is insufficient. RAG is computationally costly and requires a relevant clinical database for supporting documents.

Examples of the disclosure provide an input augmentation (IA) system that addresses these and other technical problems with LM tasks for clinical documents. More specifically, the IA system augments (e.g., edits, amends) an original document (the "input document") with named entity recognition (NER) and entity linking techniques, adding entity tags or "anchor tags" to the various named entities that appear within the input document, as well as defining features or attributes of each named entity. In addition, the IA system also performs entity filtering on the input document, limiting the entities identified in the input document to just those entities of particular interest in a given query (e.g., based on entity name, entity type, or other such attributes or features identified by the tags). The IA system thus modifies the input document into an "enhanced input document" that is then provided to a GAI model or other generative application (e.g., LM, LLM, multi-modal model, or the like), along with a relatively simple query prompt, to generate improved output of the GAI model. This “enhanced output” text more greatly focuses on the elements of interest (e.g., based on the named entity recognition and filtering), as well as embeds and repeats anchor tags in the output that can be used to reference back to the anchor tags provided in the enhanced input document, thus allowing practitioners to identify references from the original text that support particular assertions generated in the output text.

While examples are described herein with reference to LMs, aspects of the disclosure are operable with any form of generative application or GAI model that processes at least text-based input and provides output. Some examples contemplate large LMs, small (e.g., local or non-cloud) LMs, image-based models, multi-modal models, and the like.

In some examples, the IA system performs NER on the input document to identify named entities appearing within the input document. In examples, the NER process utilizes an NER model to identify clinical named entities that appear in the input document (e.g., names or types of particular diagnoses, examinations, or the like). For each named entity that appears within the input document, the IA system adds an anchor tag to the document (e.g., as markup tags surrounding the text of the named entity where it appears in the document). Further, the IA system also generates a unique identifier (ID) for each unique named entity and adds that ID to the anchor tag for each unique named entity (e.g., as an attribute name-value pair within the tag). For example, if a diagnosis of “Carcinoma” is identified as a named entity appearing within the document, the IA system generates a unique integer of “9876” to use as the entity ID for this named entity and adds opening and closing anchor tags around the “Carcinoma” text (e.g., “ . . . <entity: 9876> Carcinoma </entity> . . . ”).

In examples, the IA system also uses a clinical ontology graph to identify features or attributes of each named entity, and these features are also added to the anchor tag for that entity. For example, if the IA system uses the ontology graph to determine that “Carcinoma” is a type of diagnosis, the IA system adds a feature of “DIAGNOSIS” to that anchor tag (e.g., “ . . . <entity: 9876, DIAGNOSIS> Carcinoma </entity> . . . ”). Several such features may similarly be added to any or all of the anchor tags. For example, given that Carcinoma is a type of cancer, the feature of “CANCER” may, additionally or alternatively, be added to the anchor tag. The IA system, in some examples, uses these features to filter which named entities are tagged within the document. For example, if the user wishes to focus only on diagnoses appearing within the document, but is less interested in other content such as examination data that might appear in the document, the IA system applies filters to mask or remove any named entities with anchor tags that do not include the DIAGNOSIS attribute. As such, limiting the entity naming to only those entities having particular features allows the IA system to refine the focus of the output generated by the LM in addition to reducing the processing resource requirements of the IA system.

In these examples, the additions and changes made to the original document result in a modified document, or an “enhanced input document.” This enhanced input document is provided to the LM along with a simple query prompt that provides instruction to the LM for processing the document as desired. In examples, this query prompt includes both (A) task text that identifies the type of operation to perform on the document (e.g., perform a summary of the document, perform statistical analysis, identify particular information), as well as (B) anchoring markup text that instructs the LM how to add “reference anchor tags” to the output. This anchoring markup text both identifies the format of the anchor tags as they appear within the enhanced input document, as well as instructs the LM to add those anchor tags (and their unique entity IDs and features) whenever they appear within the LM output.

The query prompt and the enhanced input document are provided to the LM, thereby causing the LM to generate enhanced output that both performs the task of interest (e.g., as identified by the task text of the query prompt) as well as includes reference anchor tags for each particular named entity that appears in the output. For example, each time the named entity of “Carcinoma” appears in the LM output, the reference anchor tag of “[9876, DIAGNOSIS]” is included in the output just after that named entity.

The IA system and techniques described herein provide technical improvements over existing systems that attempt to leverage LMs for analyzing clinical documents. The IA system adds anchor tags to the text content of an input document, where the anchor tags include an entity ID and clinical attribute(s) associated with the clinical named entity. This addition of anchor tags helps the LM focus more specifically on particular portions of the text content (e.g., the named entities of interest, and as identified by the anchor tags). This focus reduces the computational burden and hardware requirements over conventional systems by, for example, reducing the number of iterations (e.g., reduced processor and memory usage) needed to be executed by the LM to get to a focused result. Further, some conventional systems often attempt to employ extensive pre-processing or post-processing solutions that are computationally expensive, attempting to either add extensive text to the query (e.g., in the form of additional documents for additional context, thus adding to the computational expense of the LM in processing the query) or attempting to “fix” the unfocused output with extensive computational expenses after the LM has generated the output. In contrast, by adding the anchor tags in a targeted way prior to processing, the LM as described herein can process the queries much easier (e.g., with significantly less processor and less memory usage) than in conventional systems.

The various examples are described in detail with reference to the accompanying drawings. Wherever preferable, the same reference number is used throughout the drawings to refer to the same or like parts. References made throughout this disclosure relating to specific examples and implementations are provided solely for illustrative purposes but, unless indicated to the contrary, are not meant to limit all examples.

FIG. 1 illustrates an example architecture of an input augmentation (IA) system 100 in which an IA device 110 performs various analytics tasks on clinical documents using a generative AI model, such as LM 130. In the example, the IA device 110 prepares an input document (or “original document”, “source document”) 106 for submission to the LM 130 by identifying named entities appearing within the input document 106 and adding anchor tags and features for each named entity into the document 106. This document modification process generates an enhanced input document 116 that, together with a particular query prompt 118, is submitted to the LM 130, thereby causing the LM 130 to generate enhanced output 132 that is both more focused on particular portions of the document 106 (e.g., ensuring all relevant clinical information is taken into account), and also identifies support from the input document 106 for assertions made in the output. While the example of FIG. 1 utilizes the LM 130 for processing the enhanced input document 116, it should be understood that other types of generative AI models may be used (e.g., large LMs, small (e.g., local or non-cloud) LMs, image-based models, multi-modal models, and the like).

More specifically, in the example, the input document 106 is a clinical document that includes at least some text-based content, such as admission notes, a discharge summary or discharge instructions, a radiology narrative, progress notes, nursing notes, treatment plans, medical histories, consultation reports, care coordination notes, operative reports, pathology reports, lab test results, medication reports, immunization records, referral letters, rehabilitation or therapy notes, diagnostic imaging reports, or the like. In some examples, the input document 106 is provided by a user computing device 104 of a user 102, or perhaps retrieved from a documents database 108 (e.g., of an electronic health record (EHR) system, a radiology information system (RIS), a practice management system (PMS), a health information management system (HIMS), a clinical decision support system (CDSS), or the like). In examples, it is the text content of the input document 106 that is the primary focus of the IA device 110 and the pre-processing operations described herein.

The IA device 110, in the example, performs named entity recognition (NER) and entity linking (e.g., at NER 112). NER 112 identifies named entities appearing within the input document 106. A named entity refers to a real-world object or concept that is assigned a specific name, making it identifiable and distinct within a particular context. Named entities can include, for example, people, organizations, locations, dates, quantities, and other categories of specific information that can be uniquely referenced by name in text. In clinical document examples, named entities can include, for example, medications (e.g., drug names, prescription medications, or treatments administered to the patient), medical conditions (e.g., diseases, disorders, or medical conditions affecting the patient), symptoms and signs (e.g., physical symptoms or signs observed in, or by, the patient), procedures (e.g., medical, surgical, or diagnostic procedures that have been performed or planned), anatomical locations (e.g., body parts, organs, or anatomical locations), test names (e.g., diagnostic tests or laboratory tests conducted for the patient), test results (e.g., quantitative or qualitative results of laboratory or diagnostic tests), medical devices (e.g., devices used in the diagnosis, monitoring, or treatment of the patient), dosages (e.g., dosage amounts, frequencies, and routes of administration related to medication), healthcare providers (e.g., names or titles of doctors, specialists, nurses, or other healthcare professionals involved in patient care), patient information (e.g., patient-related data, such as name, age, or demographic information), treatment plans (e.g., future or current plans for patient treatment, including follow-up care), clinical findings (e.g., observations or clinical conditions made by healthcare providers), temporal information (e.g., dates, times, or durations associated with patient care, treatments, or events), biological entities (e.g., genetic or molecular biology terms relevant to patient conditions or tests), allergies (e.g., known patient allergies to medications, food, or substances), dosage forms (e.g., specific forms in which medications are administered), lab values and measurements (e.g., numerical values, lab measurements, or other quantitative metrics), pathogens (e.g., names of particular bacteria, viruses, or other such infectious agents responsible for diseases), healthcare facilities (e.g., names of hospitals, clinics, or healthcare facilities where care is provided), or the like.

In the example, the IA device 110 uses an NER model 140 to identify such named entities appearing within the text content of the input document 106, where the NER model 140 takes a string of text as input and generates a list of zero or more named entities 142 as output (e.g., as a text string of each named entity, a unique identifier of a particular named entity, or the like). In some examples, the NER model 140 is trained to identify named entities for clinical documents (e.g., a clinical entity vocabulary or medical entity lexicon from a clinical named entity set, clinical entity schema, clinical entity ontology, and/or clinical concept ontology that includes terms that are common to this specific clinical domain). In some examples, the NER model 140 identifies spans which represent an entity (e.g., without any lexicon). In some examples, the NER 112 parses the input document 106 into sentences or paragraphs and separately sends each of these sentences or paragraphs to the NER model 140, receiving named entities 142 for each sentence or paragraph.

For each named entity 142 identified in the input document 106, the NER 112 generates a unique ID (an "entity ID") for that named entity (e.g., a unique integer or alphanumeric string). The NER 112 adds an anchor tag to each named entity within the input document and includes the particular entity ID for that named entity within the anchor tag. In examples, the anchor tag is provided as markup language that includes an opening tag (e.g., "<entity>" and a closing tag "</entity>". Further, the opening anchor tag also includes the entity ID for that named entity. For example, presume a named entity 142 of "non-contrast head CT" is identified in the input document 106 and the NER 112 assigns the integer "7263" to this named entity 142. As such, the opening anchor tag of "<entity: 7263>" is inserted before the appearance of "non-contrast head CT" in the document 106, and a closing anchor tag of "</entity>" is inserted just after (e.g., " . . . <entity: 7263> non-contrast head CT </entity> . . . "). Accordingly, for each named entity 142 identified by the NER 112, a unique entity ID is generated by the NER 112 and an anchor tag is added into the document 106 with at least that entity ID.

In some examples, when the NER 112 identifies a named entity 142 that is or otherwise includes an abbreviation or acronym of that entity in the original text, the NER 112 also adds a normalized entity name for that abbreviation or acronym into the input document 106 (e.g., as a parenthetical after the abbreviation or acronym). Continuing the above example, the "non-contrast head CT" includes the acronym "CT" (acronym for "Computed Tomography", or a Computed Tomography scan). As such, the NER 112 adds the text "(Computed Tomography)" or "(Computed Tomography scan)" immediately after the acronym. Accordingly, the named entity with anchor tag example now includes: " . . . <entity: 7263> non-contrast head CT (Computed Tomography) </entity> . . . "). In some examples, the NER model 140 identifies this named entity by its normalized name (e.g., as the named entity 142, and based on the acronym as provided by in the input text) and the NER 112 uses that output to identify the mismatch between the input text (e.g., having the acronym or abbreviation) and the output text of the named entity 142 (e.g., having the normalized name). Upon detection of this mismatch, the NER 112 generates the parenthetical for the abbreviation or acronym and thus adds the normalized entity name to the input document 106. In some examples, the NER 112 scans the input document 106 for abbreviations or acronyms (e.g., prior to submission to the NER model 140) and uses either of the NER model 140 or the clinical ontology 150 to identify the normalized name for each acronym or abbreviation identified, adding parentheticals into the input document 106 for each.

In some examples, the NER 112 also adds one or more entity features (or "attributes") 152 for some or all of the named entities identified in the input document. In the example, the NER 112 uses a clinical ontology (or "graph") 150 to identify one or more entity features 152 associated with a particular named entity. The ontology 150 includes a structured and standardized representation of concepts, terms, and relationships used in healthcare and clinical practice, and serves as a formal system to categorize and link various medical and clinical terms (e.g., named entities 142), ensuring that healthcare information is consistently defined, understood, and shared across systems, thereby helping to organize medical knowledge, enable interoperability between health information systems, and support tasks like clinical decision-making, data mining, and research, as well as the various operations described herein.

In some instances, the ontology 150 includes hierarchical structures for concepts and the NER 112 uses the ontology 150 to identify a higher-level category name for a given concept. More specifically, the NER 112 searches the ontology 150 for a particular named entity and then identifies a type or category name under which that named entity appears in the ontology 150. For the above example, presume the named entity "non-contrast head CT" appear in the ontology 150 as a type of "examination". As such, the NER 112 identifies an attribute of "EXAMINATION" for this example named entity 142. In another example, presume a named entity of "contusion", "frontal contusion", or "left frontal contusion" appears in the ontology 150 as a type of "diagnosis". As such, NER 112 identifies an attribute of "DIAGNOSIS" for this particular named entity 142. Such an attribute is used as one of the entity features 152 for that particular named entity 142.

In such examples, the NER 112 adds one or more entity features 152 to the anchor tag for the associated named entity 142. These entity features 152 are added as additional key words to the anchor tag (e.g., as a comma-delimited list after the "entity: ID" component). For example, for the "left frontal contusion" named entity introduced above, the term "EXAMINATION" is identified from the ontology 150 based on the named entity and is added to the anchor tag (e.g., " . . . <entity: 7263, EXAMINATION> left frontal contusion </entity> . . . "). Accordingly, one or more entity features 152 may be added to any or all of the named entities 142 identified by the NER 112.

In some examples, the NER model 140 also generates one or more features associated with the named entity 142 (e.g., "DIAGNOSIS", "EXAMINATION"). In some examples, the attributes provided by the NER model 140 or from the ontology 150 include any of normalized entity name (e.g., the official name of the entity in the ontology, such as "Coronary Artery Disease" for "CAD"), or the hierarchical parent name (e.g., the "parent" of the term within the ontology 150, such as "cancer" as the parent of the term "carcinoma"). In some examples, attributes determined from the NER model 140 and/or the ontology 150 are added to the anchor tags.

In some examples, the NER model 140 also generates a confidence score for each identified named entity 142. The confidence score represents a determination as to the likelihood that the named entity 142 actually matches the input provided to the model 140 (e.g., a likelihood between 0.0 and 1.0 as to whether the named entity 142 actually appears in the input text). In some examples, if the context score for a given named entity 142 is below a preconfigured threshold, then that named entity 142 is excluded (e.g., is not considered a named entity in the input document 106, and thus does not have an anchor tag created).

In some examples, the NER 112 adds a new (e.g., unique) entity ID for each named entity 142 identified in the input document 106 (e.g., a unique ID per occurrence). In some examples, the NER 112 performs a co-reference algorithm that detects when two or more named entities 142 are referring to the same thing (e.g., the same examination, the same diagnosis). For example, the NER 112 identifies same-named entities 142, such as two or more different occurrences of "left frontal contusion", and inspects each set of such same-named entities 142 (the multiple instances appearing in the input document 106) for whether they refer to the same "left frontal contusion". In some examples, the NER 112 determines a date/time associated with each separate instance and uses those date/times to determine whether they refer to the same instance. In some examples, the NER 112 analyzes context surrounding each occurrence, such as reason for the exam, location or setting (e.g., inpatient vs. outpatient), or findings or results and correlates or excludes based on such context. In some examples, the NER 112 analyzes proximity of one occurrence to another occurrence within the input document 106 (e.g., with smaller textual distance between occurrences indicating higher likelihood of referring to the same entity). In some examples, any or all references to the same named entity 142 are considered as referring to the same entity. In some examples, the NER 112 uses the ontology 150 to provide an additional attribute of correlation ID even if the term appears in different forms (e.g., mentions use of different synonyms of the same concept).

In some examples, the IA device 110 also implements an entity filter 114. The entity filter 114 is configured to restrict the creation of anchor tags for only certain named entities. In this example, a set of one or more filters 160 are implemented by the entity filter 114. These filters 160 define what type(s) of named entities are to be included in the anchor tagging process (e.g., as inclusion criteria), or, additionally or alternatively, what type(s) of named entities are to be excluded from anchor tagging (e.g., as exclusion criteria). In examples, each filter 160 identifies one or more attributes (e.g., certain entity features 152 from the ontology 150) that will cause any such named entities to have an anchor tag added into the document 106. In other words, in the "inclusion" embodiment, if a particular named entity 142 has an entity feature 152 that matches the criteria of a filter 160, then the IA device 110 adds an anchor tag to the document 106 for that particular named entity 142. Likewise, in the "exclusion" embodiment, the IA device 110 does not add an anchor tag to the document 106 for a particular named entity 142 if the associated entity feature(s) 152 of that named entity 142 match the criteria of a filter 160 (e.g., or removing already-created anchor tags that match exclusion criteria). In some examples, the filter 160 uses any or all of: hierarchical information (e.g., filter entities 142 by leaving only terms that are part of a sub-tree within the ontology 150, such as "cancer" or "pain medications"); ontology relations (e.g., ontologies usually contain information about relations that a particular entity 142 is connected to, thus may filter the entities 142 by asking to mark only entities that are connected to "X cures Y" relations); and assertion (e.g., for examples where the NER model 140 generates assertions for each entity, such as Positive, Negative, Neutral, filtration may also be performed on this criterion).

While the NER 112 and entity filter 114 are illustrated in FIG. 1 as separate processes for ease of description, it should be understood that the filtration processes can be integrated into the operations of the NER 112. For example, the NER 112 may implement the filters 160 before any anchor tags are added into the document 106.

After the NER 112 and entity filtering 114 described above, the IA device 110 has modified the input document 106 with at least anchor tags, resulting in an enhanced input document 116. In other words, the enhanced input document 116 includes the text content of the input document 106, as well as the anchor tags added by the NER 112 and entity filter 114 as described above.

In the example, this enhanced input document 116 is provided as one input component to the LM 130. In addition, the IA device 110 also provides a query prompt 118 as another input component to the LM 130. The query prompt 118 includes two sub-components, namely, a task component and an anchoring markup component. The task component of the query prompt 118 includes task text that defines what task is to be performed on the enhanced input document 116 (e.g., "Simplify the following clinical text", "Identify all medications prescribed in the following clinical text"). The anchoring markup component is text that instructs the LM as to how to use the anchor tags (as appearing in the enhanced input document) and how to include references to those anchor tags for entities when they appear in the LM output (e.g., the enhanced output 132). Additional details for the query prompt 118 and its sub-components as well as the references are described in greater detail below with regard to FIG. 2A and FIG. 2B.

As such, in the example, the IA device 110 submits the query prompt 118 and the enhanced input document 116 to the LM 130 for processing, thereby causing the LM 130 to generate the enhanced output 132. Since the query prompt 118 included instructions on the task to be performed on the enhanced input document 116, as well as how to interpret the anchor tags and instructions to include the entity IDs in the output 132, the enhanced output 132 thus includes the output of the task as performed by the LM 130, but also includes references (or "reference anchor tags") for each tagged named entity that appears in the output 132, thereby allowing the IA device 110 and/or the user 102 to use those entity IDs to reference back to the enhanced input document 116 (e.g., for researching supporting information, verifying assertions in the output, verifying inclusion of each of the tagged named entities in the output 132, or the like).

In some examples, the IA device 110 automatically analyzes the enhanced output 132 from a particular task via corrections analysis 120. In some examples, corrections analysis 120 includes identifying whether all of the tagged named entities from the enhanced input document 116 appear somewhere in the enhanced output 132 (e.g., to protect against "lost in the middle" errors). If one or more tagged named entities do not appear in the output 132, then corrections analysis 120 generates an additional query prompt 118 that asks the LM 130 to incorporate that particular tagged named entity into the analysis and regenerate the enhanced output 132 (e.g., within the same context as the earlier submission(s)).

In examples, the IA device 110 displays the enhanced output 132 to the user 102 via user computing device 104. More specifically, the IA device 110 presents a user interface (UI) 122 that allows the user 102 to view the enhanced output 132, as well as interact with other features of the IA device 110 (e.g., defining filters 160, identifying tasks for the query prompt 118, or the like). In some examples, the IA device 110 edits the enhanced output 132 prior to display to the user 102, removing all reference anchor tags from the enhanced output 132. In some examples, the IA device 110 presents the enhanced output 132 with the reference anchor tags included, and additionally allows the user 102 to view the enhanced input document 116 (which includes the anchor tags). As such, the user 102 can use the entity IDs appearing in the reference anchor tags of the enhanced output 132 to refer back to the enhanced input document 116, thereby allowing the user 102 to identify where that named entity appeared in the original document. In some examples, the UI 122 may provide hotlinks or mouse-over functionality that causes the UI 122 to automatically display or redirect to an associated location in the enhanced input document 116 when the user 102 clicks on or mouses over a reference anchor tag while viewing the enhanced output 132 (e.g., searching the enhanced input document 116 for the entity ID with which the user 102 is interacting).

In some examples, the IA device 110 additionally performs document preparation tasks on the input document 106 (e.g., prior to NER 112) to, for example, identify and correct typographical errors in the input document 106, identify and expand acronyms that appear in the input document 106.

While one example architecture is shown in FIG. 1 for the IA system 100 and associated functionality described herein, it should be understood that other architectures are possible. For example, the IA system 100 can be provided in a virtual environment or cloud environment, in a client-server architecture (e.g., exposing an application programming interface (API) 124 for interaction with other client systems), and/or in an "as a service" architecture.

Figure 2A:
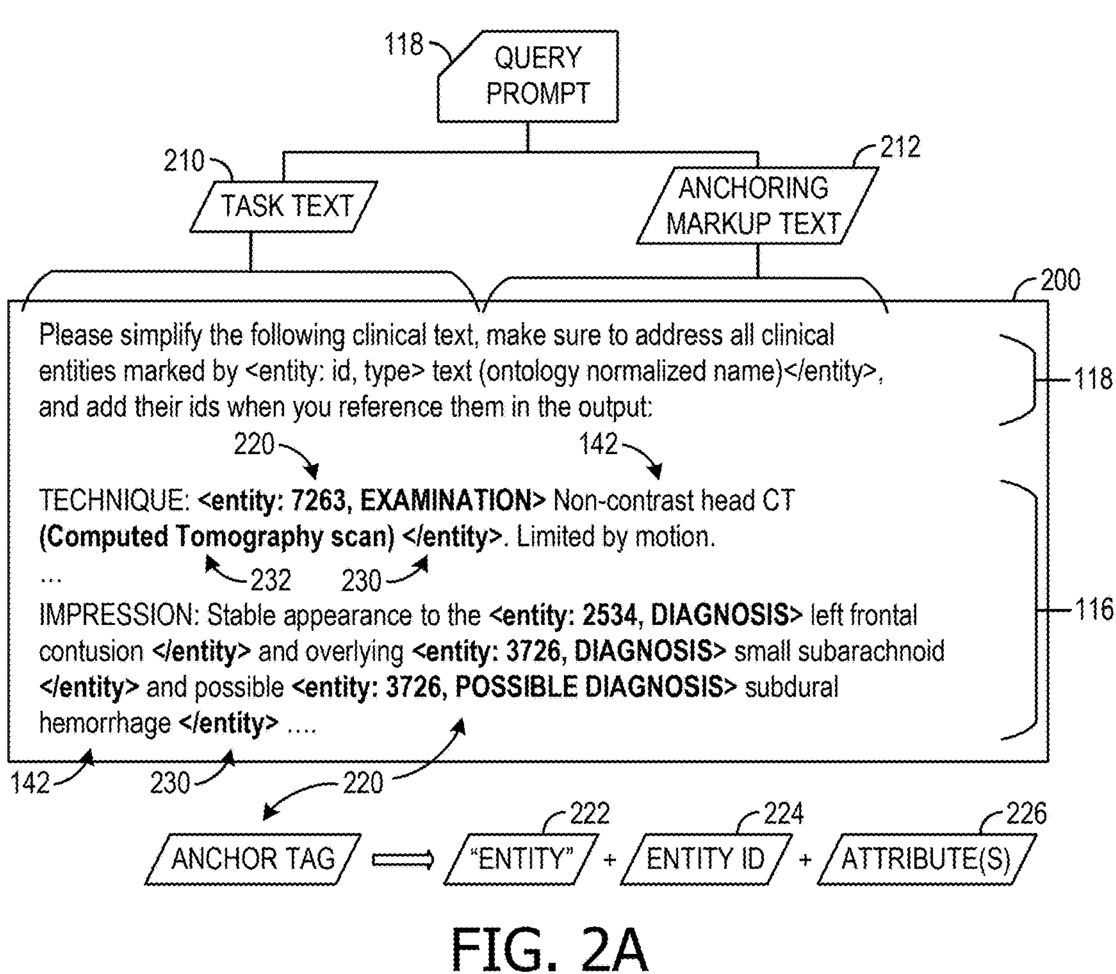
FIG. 2A illustrates an example administrative screen of the IA system in which components of an example query prompt are displayed along with text of an example enhanced input document.

FIG. 2A illustrates an administrative screen 200 of the IA system 100 in which components of an example query prompt 118 are displayed along with text of an example enhanced input document 116. In the example screen 200, example text of the query prompt 118 is shown above example text of the enhanced input document 116.

More specifically, in the example, the query prompt 118 includes two components, namely task text 210 and anchoring markup text 212. The task text 210 represents instructions on the task to be performed by the LM 130 on the enhanced input document 116. In this example, the task text 210 recites: "Please simply the following clinical text, . . . ." In other words, the task text 210 is requesting a summarization of the example enhanced input document 116, which is the "following clinical text" referred to by the task text 210. The anchoring markup text 212 represents structural details about how the named entities are marked up (within the "following clinical text", namely, the enhanced input document 116), as well as instruction to add the entity IDs whenever they are referenced in the output (e.g., in the enhanced output 132). In this example, the anchoring markup text 212 recites: " . . . , make sure to address all clinical entities marked by <entity: id, type> text (ontology normalized name) </entity>, and add their ids when you reference them in the output: . . . ."

In the example text of the enhanced input document 116, note that several named entities 142 are present in the example. Example named entities include "non-contrast head CT", "left frontal contusion", "small subarachnoid", and "subdural hemorrhage" (only some of which are numbered in FIG. 2A for clarity). Further, each example named entity 142 is preceded by an opening anchor tag 220 and a closing anchor tag 230. FIG. 2A also illustrates the structure of opening anchor tags 220 as including the keyword "entity" 222, the entity ID 224, and optionally one or more attributes 226. For example, the named entity 142 of "subdural hemorrhage" has an opening anchor tag of "<entity:

3726, POSSIBLE DIAGNOSIS>", where the entity ID for this named entity 142 is assigned as the value 3726, and where one attribute 226 of "POSSIBLE DIAGNOSIS" is included for this named entity 142.

Also shown in the example is a normalized entity name added as a parenthetical 232 behind the acronym "CT" in the enhanced input document 116. More specifically, the NER 112 detected the presence of the acronym "CT", determined the normalized entity name of "Computed Tomography scan" for CT (e.g., from output of the NER model 140, from the clinical ontology 150), and added the parenthetical 132 of "(Computed Tomography scan)" behind the acronym and within the anchor tag 220 for that named entity 142 "Non-contrast head CT".

Figure 2B:
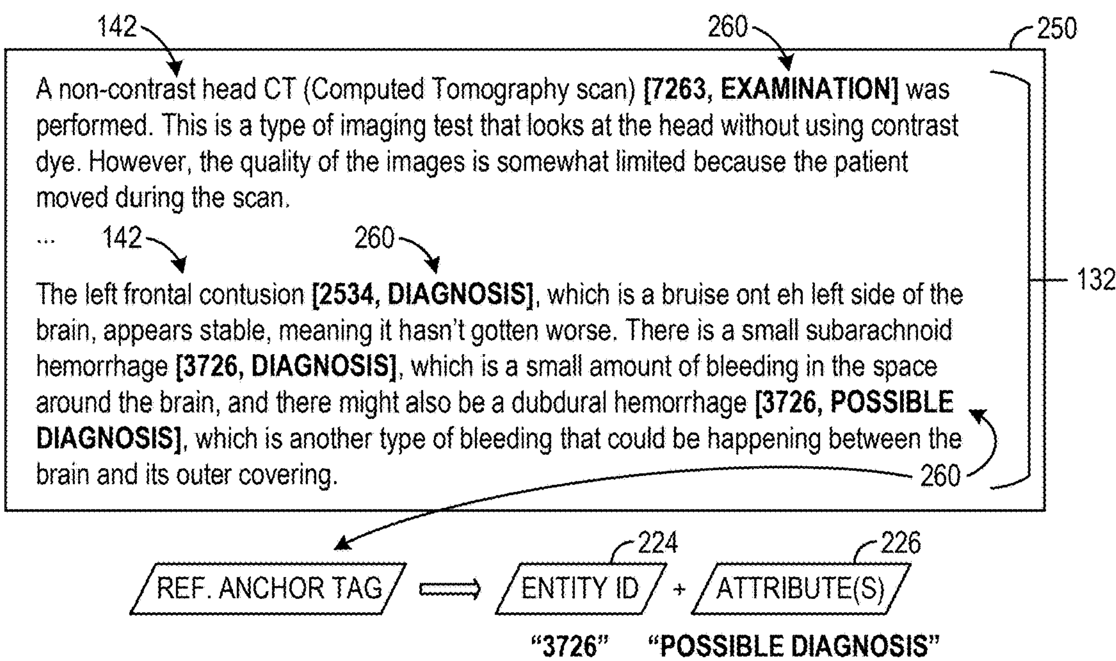
FIG. 2B illustrates an example administrative screen in which example enhanced output of the LM is shown.

FIG. 2B illustrates an administrative screen 250 in which example enhanced output 132 of the LM 130 is shown. In this example, it is presumed that this enhanced output 132 is the output generated by the LM 130 after processing the query prompt 118 shown in FIG. 2A. Note that the enhanced output 132 includes several reference anchor tags 260, each of which has been added (e.g., automatically by the LM 130 in response to the instructions of the anchoring markup text 212) just after the named entity with which it is associated. FIG. 2B also illustrates the structure of reference anchor tags 260 as including the entity ID 224 of the named entity 142 and optionally one or more attributes 226 (e.g., as a bracketed, comma-delimited list appearing after the named entity 142). In some examples, either or both of the screens 200, 250 may be displayed via the UI 122 of FIG. 1 (e.g., to the user 102).

Figure 3:
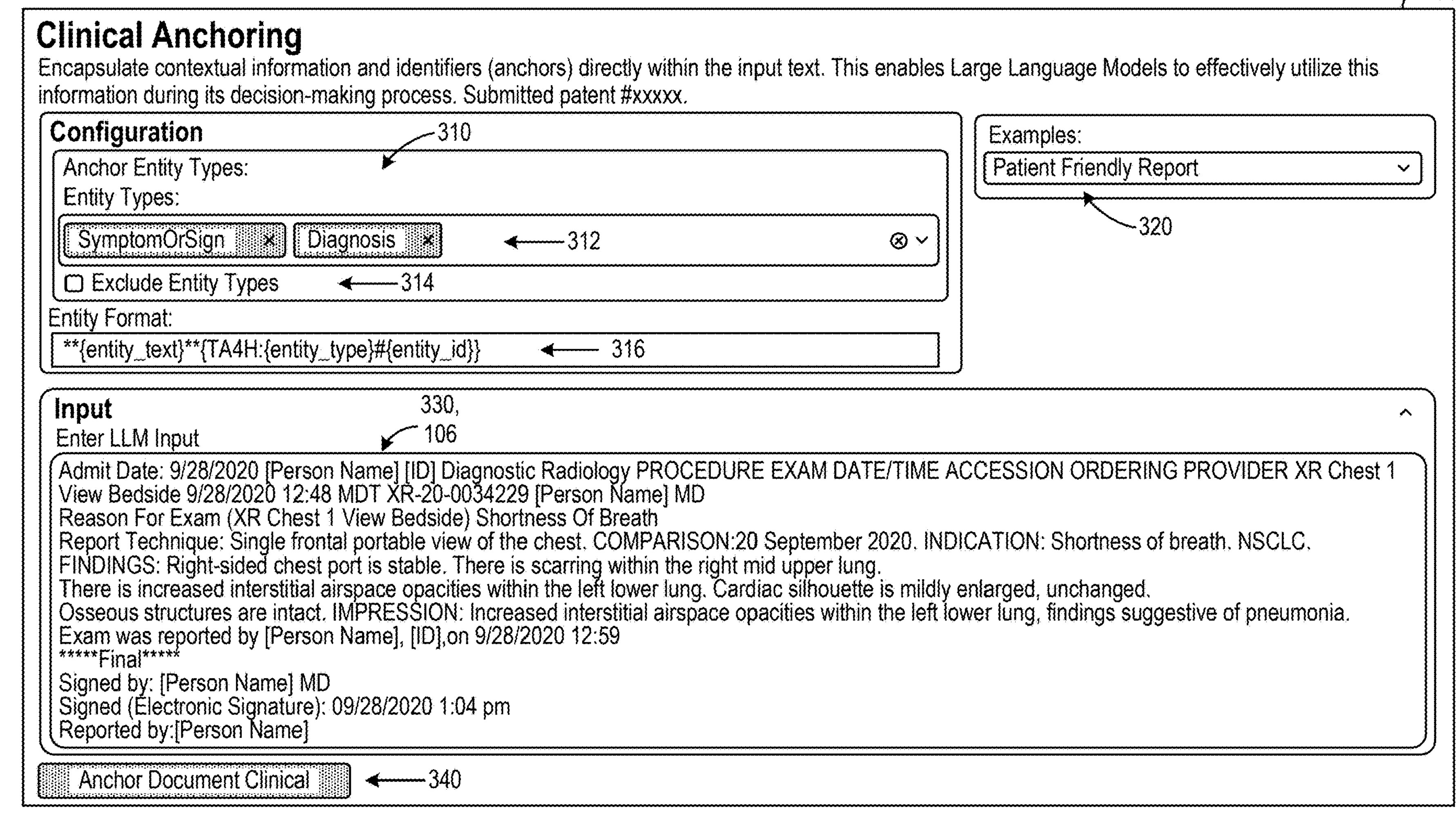
FIG. 3 is an example screen presented by the user interface to the user in the IA system of FIG. 1.

FIG. 3 is an example screen 300 presented by the UI 122 to the user 102 in the IA system 100 of FIG. 1. In the example, the screen 300 allows the user 102 to submit an input document (e.g., text content to be analyzed by the LM 130) to the IA system 100, as well as configure several features of the requested task. The example screen 300 includes an entity filters section 310 in which the user 102 adds or removes filters 160 for this task ("entity types" 312 of "SymptomOrSign" and "Diagnosis" in this example). The filters section 310 also includes a filtration toggle button 314 that switches the filtration process from an "inclusion" type filter (e.g., when unmarked) to an "exclusion" type filter (e.g., when marked), as described above in reference to FIG. 1. The example screen 300 also includes a task dropdown 320 in which the user 102 selects what type of task they wish to perform (e.g., from a preconfigured set of example tasks, where each task includes a preconfigured task text 210 to be used in the query prompt 118).

In the example, the screen 300 also includes an entity format box 316 in which a template for the anchor tags is defined. In this example, the entity format box 316 currently displays: {entity_text} [TA4H: {entity_type}#{entity_id}]. Here, '{entity_text}' represents the name of the particular named entity 142 (e.g., with the addition of '' both before and after the name), 'TA4H' is a special keyword used for this particular type of tag (e.g., in lieu of "entity" 222 as used in many of the above examples), '{entity_type}' is a type identifier for the particular entity (e.g., an example entity feature 152 of FIG. 1, attribute 226 of FIG. 2A), and '{entity_id}' is the entity ID for the particular named entity 142 (e.g., the entity ID 224 of FIG. 2A). As such, upon submission of this example task, the IA device 110 uses the template shown in the entity format box 316 when creating anchor tags 220**.

The screen 300 also provides an input section 330 in which text content to be analyzed is displayed. The text in this input section 330 represents the text of the input document 106 of FIG. 1. In some examples, the screen 300 may allow the user 102 to enter text into the input section (e.g., via copy/paste from the input document 106 of interest to the user 102). In some examples, the screen 300 may allow the user 102 to identify the input document 106 (e.g., from the documents database 108, dragging and dropping the input document 106 onto the input section 300, or the like). Note that the example text shown in input section 330 of FIG. 3 does not yet include any anchor tags.

In the example, once the user 102 has completed the configuration selections on the screen 300, the user 102 activates an "anchor clinical document" button 340, thereby causing the IA device 110 to perform the NER 112 and entity filter 114 processes as shown in FIG. 1, thus resulting in the enhanced input document 116.

FIG. 4 illustrates example text of enhanced input document 116 in an output section 400 after anchor tags have been added to the example input document 106 shown in input section 330 of FIG. 3. In the example, after the user 102 configures and initiates the task as described in FIG. 3, the IA device 110 analyzes the example input document 106 in input section 330, identifies various named entities 142 appearing within, as well as their associated entity type (e.g., based on the ontology 150), and adds anchor tags 220 to the input document 106 in input section 330 (for each named entity 142 that passes the filters 160). The resulting enhanced input document 116 shown in output section 400 thus includes several "SymptomOrSign" and "Diagnosis" anchor tags, as included in the configuration of the entity types 312 to be included in FIG. 3.

One example named entity 142 and associated anchor tag 220 is shown in greater detail in FIG. 4. The example named entity 142 of " Shortness of Breath " appears early on in the enhanced input document 116 in output section 400. The example anchor tag 410 added to the enhanced input document 116 in output section 400 includes a tag name 410 (e.g., "TA4H"), an attribute 226 (e.g., "SymptomOrSign", as an entity type), and an entity ID 224 (e.g., "3db09d36").

FIG. 5 is a flowchart 500 illustrating exemplary operations performed by the IA system 100 of FIG. 1 for augmenting clinical documents to guide generative AI in analytics of clinical documents. In examples, the operations are performed by the IA device 110 on the input document 106 shown in FIG. 1. At operation 510, the IA device 110 identifies a clinical named entity (e.g., named entity 142) within text content of a clinical input document (e.g., input document 106). At operation 512, the IA device 110 adds an anchor tag (e.g., anchor tag 220) to the text content, the anchor tag including an entity ID (e.g., entity ID 224) and a clinical attribute (e.g., attribute 226) associated with the clinical named entity, thereby generating an enhanced input document (e.g., enhanced input document 116). At operation 514, the IA device 110 submits a first query prompt (e.g., query prompt 118) and the enhanced input document to a LM (e.g., LM 130), the first query prompt including task text (e.g., task text 210) and anchoring markup text (e.g., anchoring markup text 212), the task text includes instructions of a task to be performed by the LM on the enhanced input document, the anchoring markup text includes a template of the anchor tag and instruction to add a reference anchor tag to output generated by the LM, where the reference anchor tag is to include the entity ID and the clinical attribute of the anchor tag.

In some examples, the IA device 110 searches a clinical ontology (e.g., ontology 150) for the clinical named entity and identifies the clinical attribute as an entity type of the clinical named entity, the entity type being a parent of the clinical named entity within a hierarchy of the clinical ontology. In some examples, the IA device 110 determines that the clinical named entity satisfies a clinical criterion (e.g., filter 160) based on the clinical attribute of the clinical named entity, wherein adding the anchor tag to the text content is based on the determining.

In some examples, the IA device 110 submits at least a portion of the text content to a named entity recognition (NER) model (e.g., NER model 140), the NER model being trained on a vocabulary of clinical entities and configured to output names of named entities appearing within input text. In response, the IA device 110 receives, as output from the NER model 140, the named entity (and optionally one or more attributes), and identifies an occurrence of the named entity within the text content, wherein adding the anchor tag includes adding the anchor tag one of before, after, or around the occurrence of the named entity within the text content.

In some examples, the IA device 110 receives output text (e.g., enhanced output 132) from the LM in response to the submitting, determines that the output text does not include a reference to the entity ID of the clinical named entity, and submits a second query prompt to the LM, the second query prompt instructing the LM to update the output text to include a reference to the entity ID.

In some examples, the IA device 110 receives output text from the LM in response to the submitting, the output text including a reference anchor tag (e.g., reference anchor tag 260), the reference anchor tag including the entity ID associated with the clinical named entity, transmits the output text to another computing device (e.g., user computing device 104) for display via a user interface, receives user input identifying the reference anchor tag, in response to the user input, searches the text content of the clinical input document for the anchor tag based on the entity ID appearing in the reference anchor tag, and transmits at least a portion of the text content around the anchor tag to the other computing device for display via the user interface.

In some examples, the IA device 110 causes a query configuration screen (e.g., screen 300) to be displayed via a user interface (e.g., UI 122), the query configuration screen including one or more of a filter criteria section (e.g., section 310), a tag format section (e.g., entity format box 316), a task selection section (e.g., task dropdown 320), and an input text section (e.g., input section 330), the filter criteria section allowing configuration of a first filter criterion, the tag format section allowing configuration of the template, the task selection section allowing selection of a task, the input text section allowing input of the text content.

Additional Examples

While described with reference to the input being text, aspects of the disclosure are operable with the input being one or more images, such as in a radiology report. In such examples, aspects of the disclosure identify objects in the image, and confirm that text entities are mapped to corresponding image entities, to help focus the practitioner on particular aspects of the input images.

An example input augmentation system for analyzing clinical documents comprises: a processor; and a computer-readable medium storing instructions that are operative upon execution by the processor to: identify a clinical named entity within text content of a clinical input document; add an anchor tag to the text content, the anchor tag including an entity ID and a clinical attribute associated with the clinical named entity, thereby generating an enhanced input document; and submit a first query prompt and the enhanced input document to a LM, the first query prompt including task text and anchoring markup text, the task text includes instructions of a task to be performed by the LM on the enhanced input document, the anchoring markup text includes a template of the anchor tag and instruction to add a reference anchor tag to output generated by the LM, where the reference anchor tag is to include the entity ID and the clinical attribute of the anchor tag.

An example computer-implemented method of augmenting text inputs for analyzing clinical documents comprises: identifying a clinical named entity within text content of a clinical input document; adding an anchor tag to the text content, the anchor tag including an entity ID and a clinical attribute associated with the clinical named entity, thereby generating an enhanced input document; and submitting a first query prompt and the enhanced input document to a LM, the first query prompt including task text and anchoring markup text, the task text includes instructions of a task to be performed by the LM on the enhanced input document, the anchoring markup text includes a template of the anchor tag and instruction to add a reference anchor tag to output generated by the LM, where the reference anchor tag is to include the entity ID and the clinical attribute of the anchor tag.

An example computer storage device has computer-executable instructions stored thereon, which, on execution by a computer, cause the computer to perform operations comprising: identifying a clinical named entity within text content of a clinical input document; adding an anchor tag to the text content, the anchor tag including an entity ID and a clinical attribute associated with the clinical named entity, thereby generating an enhanced input document; and submitting a first query prompt and the enhanced input document to a LM, the first query prompt including task text and anchoring markup text, the task text includes instructions of a task to be performed by the LM on the enhanced input document, the anchoring markup text includes a template of the anchor tag and instruction to add a reference anchor tag to output generated by the LM, where the reference anchor tag is to include the entity ID and the clinical attribute of the anchor tag.

Alternatively, or in addition to the other examples described herein, examples include any combination of the following:

- identifying a clinical named entity within text content of a clinical input document;
- adding an anchor tag to the text content;
- the anchor tag including an entity ID associated with a clinical named entity;
- the anchor tag including a clinical attribute associated with the clinical named entity;
- adding an anchor tag to a clinical input document generates an enhanced input document;
- submitting a first query prompt and the enhanced input document to a LM;
- submitting a first query prompt and the enhanced input document to a GAI model;
- the first query prompt including task text and anchoring markup text;
- task text includes instructions of a task to be performed by the LM on the enhanced input document;
- task text includes instructions of a task to be performed by the GAI model on the enhanced input document;
- anchoring markup text includes a template of the anchor tag and instruction to add a reference anchor tag to output generated by the LM;

anchoring markup text includes a template of the anchor tag and instruction to add a reference anchor tag to output generated by the GAI model;

the reference anchor tag is includes the entity ID and the clinical attribute of the anchor tag;

searching a clinical ontology for the clinical named entity;

identifying the clinical attribute as an entity type of the clinical named entity;

the entity type is a parent of the clinical named entity within a hierarchy of the clinical ontology;

determining that the clinical named entity satisfies a clinical criterion based on the clinical attribute of the clinical named entity;

adding the anchor tag to the text content is based on determining that the clinical named entity satisfies a clinical criterion;

submitting at least a portion of the text content to a named entity recognition (NER) model;

the NER model is trained on a vocabulary of clinical entities;

the NER model is configured to output names of named entities appearing within input text;

receiving, as output from the NER model, the named entity;

identifying an occurrence of the named entity within the text content;

adding the anchor tag includes adding the anchor tag one of before, after, or around the occurrence of the named entity within the text content;

receiving output text from the LM in response to the submitting;

determining that the output text does not include a reference to the entity ID of the clinical named entity;

submitting a second query prompt to the LM, the second query prompt instructing the LM to update the output text to include a reference to the entity ID;

submitting a second query prompt to the GAI model, the second query prompt instructing the GAI model to update the output text to include a reference to the entity ID;

receiving output text from the LM in response to the submitting;

receiving output text from the GAI model in response to the submitting;

the output text including a reference anchor tag;

the reference anchor tag including the entity ID associated with the clinical named entity;

transmitting the output text to another computing device for display via a user interface;

receiving user input identifying the reference anchor tag;

in response to the user input, searching the text content of the clinical input document for the anchor tag based on the entity ID appearing in the reference anchor tag;

transmitting at least a portion of the text content around the anchor tag to the other computing device for display via the user interface;

causing a query configuration screen to be displayed via a user interface; and the query configuration screen including one or more of a filter criteria section, a tag format section, a task selection section, and an input text section, the filter criteria section allowing configuration of a first filter criterion, the tag format section allowing configuration of the template, the task selection section allowing selection of a task, the input text section allowing input of the text content.

While the aspects of the disclosure have been described in terms of various examples with their associated operations, a person skilled in the art would appreciate that a combination of operations from any number of different examples is also within scope of the aspects of the disclosure.

Example Operating Environment

Figure 6:
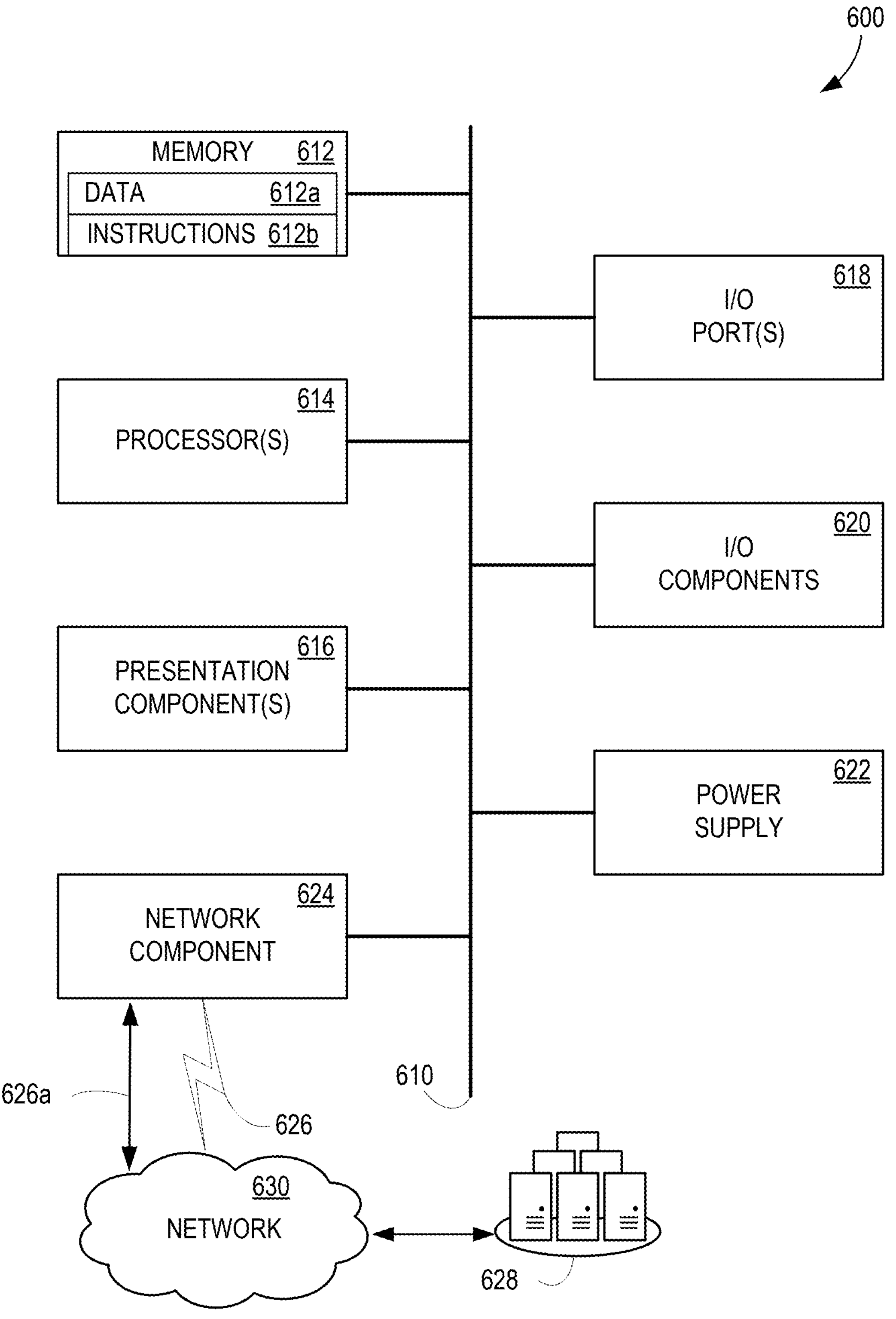
FIG. 6 is a block diagram of an example computing device (e.g., a computer storage device) for implementing aspects disclosed herein.

FIG. 6 is a block diagram of an example computing device 600 (e.g., a computer storage device) for implementing aspects disclosed herein and is designated generally as computing device 600. In some examples, one or more computing devices 600 are provided for an on-premises computing solution. In some examples, one or more computing devices 600 are provided as a cloud computing solution. In some examples, a combination of on-premises and cloud computing solutions are used. Computing device 600 is but one example of a suitable computing environment and is not intended to suggest any limitation as to the scope of use or functionality of the examples disclosed herein, whether used singly or as part of a larger set. Neither should computing device 600 be interpreted as having any dependency or requirement relating to any one or combination of components/modules illustrated.

The examples disclosed herein may be described in the general context of computer code or machine-useable instructions, including computer-executable instructions such as program components, being executed by a computer or other machine, such as a personal data assistant or other handheld device. Generally, program components including routines, programs, objects, components, data structures, and the like, refer to code that performs particular tasks, or implement particular abstract data types. The disclosed examples may be practiced in a variety of system configurations, including personal computers, laptops, smart phones, mobile tablets, hand-held devices, consumer electronics, specialty computing devices, etc. The disclosed examples may also be practiced in distributed computing environments when tasks are performed by remote-processing devices that are linked through a communications network.

Computing device 600 includes a bus 610 that directly or indirectly couples the following devices: computer storage memory 612, one or more processors 614, one or more presentation components 616, input/output (I/O) ports 618, I/O components 620, a power supply 622, and a network component 624. While computing device 600 is depicted as a seemingly single device, multiple computing devices 600 may work together and share the depicted device resources. For example, memory 612 may be distributed across multiple devices, and processor(s) 614 may be housed with different devices.

Bus 610 represents what may be one or more busses (such as an address bus, data bus, or a combination thereof). Although the various blocks of FIG. 6 are shown with lines for the sake of clarity, delineating various components may be accomplished with alternative representations. For example, a presentation component such as a display device is an I/O component in some examples, and some examples of processors have their own memory. Distinction is not made between such categories as "workstation," "server," "laptop," "hand-held device," etc., as all are contemplated within the scope of FIG. 6 and the references herein to a "computing device." Memory 612 may take the form of the computer storage media referenced below and operatively provide storage of computer-readable instructions, data structures, program modules and other data for the computing device 600. In some examples, memory 612 stores one or more of an operating system, a universal application platform, or other program modules and program data. Memory 612 is thus able to store and access data 612*a* and instructions 612*b* that are executable by processor 614 and configured to carry out the various operations disclosed herein.

In some examples, memory 612 includes computer storage media. Memory 612 may include any quantity of memory associated with or accessible by the computing device 600. Memory 612 may be internal to the computing device 600 (as shown in FIG. 6), external to the computing device 600 (not shown), or both (not shown). Additionally, or alternatively, the memory 612 may be distributed across multiple computing devices 600, for example, in a virtualized environment in which instruction processing is carried out on multiple computing devices 600. For the purposes of this disclosure, "computer storage media," "computer-storage memory," "memory," and "memory devices" are synonymous terms for the computer-storage memory 612, and none of these terms include carrier waves or propagating signaling.

Processor(s) 614 may include any quantity of processing units that read data from various entities, such as memory 612 or I/O components 620. Specifically, processor(s) 614 are programmed to execute computer-executable instructions for implementing aspects of the disclosure. The instructions may be performed by the processor, by multiple processors within the computing device 600, or by a processor external to the client computing device 600. In some examples, the processor(s) 614 are programmed to execute instructions such as those illustrated in the flow charts discussed below and depicted in the accompanying drawings. Moreover, in some examples, the processor(s) 614 represent an implementation of analog techniques to perform the operations described herein. For example, the operations may be performed by an analog client computing device 600 and/or a digital client computing device 600. Presentation component(s) 616 present data indications to a user or other device. Exemplary presentation components include a display device, speaker, printing component, vibrating component, etc. One skilled in the art will understand and appreciate that computer data may be presented in a number of ways, such as visually in a graphical user interface (GUI), audibly through speakers, wirelessly between computing devices 600, across a wired connection, or in other ways. I/O ports 618 allow computing device 600 to be logically coupled to other devices including I/O components 620, some of which may be built in. Example I/O components 620 include, for example but without limitation, a microphone, joystick, game pad, satellite dish, scanner, printer, wireless device, etc.

Computing device 600 may operate in a networked environment via the network component 624 using logical connections to one or more remote computers. In some examples, the network component 624 includes a network interface card and/or computer-executable instructions (e.g., a driver) for operating the network interface card. Communication between the computing device 600 and other devices may occur using any protocol or mechanism over any wired or wireless connection. In some examples, network component 624 is operable to communicate data over public, private, or hybrid (public and private) using a transfer protocol, between devices wirelessly using short range communication technologies (e.g., near-field communication (NFC), Bluetooth™ branded communications, or the like), or a combination thereof. Network component 624 communicates over wireless communication link 626 and/or a wired communication link 626*a* to a remote resource 628 (e.g., a cloud resource) across network 630. Various different examples of communication links 626 and 626*a* include a wireless connection, a wired connection, and/or a dedicated link, and in some examples, at least a portion is routed through the internet.

Although described in connection with an example computing device 600, examples of the disclosure are capable of implementation with numerous other general-purpose or special-purpose computing system environments, configurations, or devices. Examples of well-known computing systems, environments, and/or configurations that may be suitable for use with aspects of the disclosure include, but are not limited to, smart phones, mobile tablets, mobile computing devices, personal computers, server computers, hand-held or laptop devices, multiprocessor systems, gaming consoles, microprocessor-based systems, set top boxes, programmable consumer electronics, mobile telephones, mobile computing and/or communication devices in wearable or accessory form factors (e.g., watches, glasses, headsets, or earphones), network PCs, minicomputers, mainframe computers, distributed computing environments that include any of the above systems or devices, virtual reality (VR) devices, augmented reality (AR) devices, mixed reality devices, holographic device, and the like. Such systems or devices may accept input from the user in any way, including from input devices such as a keyboard or pointing device, via gesture input, proximity input (such as by hovering), and/or via voice input.

Examples of the disclosure may be described in the general context of computer-executable instructions, such as program modules, executed by one or more computers or other devices in software, firmware, hardware, or a combination thereof. The computer-executable instructions may be organized into one or more computer-executable components or modules. Generally, program modules include, but are not limited to, routines, programs, objects, components, and data structures that perform particular tasks or implement particular abstract data types. Aspects of the disclosure may be implemented with any number and organization of such components or modules. For example, aspects of the disclosure are not limited to the specific computer-executable instructions or the specific components or modules illustrated in the figures and described herein. Other examples of the disclosure may include different computer-executable instructions or components having more or less functionality than illustrated and described herein. In examples involving a general-purpose computer, aspects of the disclosure transform the general-purpose computer into a special-purpose computing device when configured to execute the instructions described herein.

By way of example and not limitation, computer readable media comprise computer storage media and communication media. Computer storage media include volatile and nonvolatile, removable and non-removable memory implemented in any method or technology for storage of information such as computer readable instructions, data structures, program modules, or the like. Computer storage media are tangible and mutually exclusive to communication media. Computer storage media are implemented in hardware and exclude carrier waves and propagated signals. Computer storage media for purposes of this disclosure are not signals. Exemplary computer storage media include hard disks, flash drives, solid-state memory, phase change random-access memory (PRAM), static random-access memory (SRAM), dynamic random-access memory (DRAM), other types of random-access memory (RAM), read-only memory (ROM), electrically erasable programmable read-only memory (EEPROM), flash memory or other memory technology, compact disk read-only memory (CD-ROM), digital versatile disks (DVD) or other optical storage, magnetic cassettes, magnetic tape, magnetic disk storage or other magnetic storage devices, or any other non-transmission medium that may be used to store information for access by a computing device. In contrast, communication media typically embody computer readable instructions, data structures, program modules, or the like in a modulated data signal such as a carrier wave or other transport mechanism and include any information delivery media.

The order of execution or performance of the operations in examples of the disclosure illustrated and described herein is not essential, and may be performed in different sequential manners in various examples. For example, it is contemplated that executing or performing a particular operation before, contemporaneously with, or after another operation is within the scope of aspects of the disclosure. When introducing elements of aspects of the disclosure or the examples thereof, the articles "a," "an," "the," and "said" are intended to mean that there are one or more of the elements. The terms "comprising," "including," and "having" are intended to be inclusive and mean that there may be additional elements other than the listed elements. The term "exemplary" is intended to mean "an example of." The phrase "one or more of the following: A, B, and C" means "at least one of A and/or at least one of B and/or at least one of C."

Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

What is claimed is:

1. An input augmentation system for analyzing clinical documents, the input augmentation system comprising:

a processor; and a computer-readable medium storing instructions that are operative upon execution by the processor to:

identify a clinical named entity within text content of a clinical input document;

add an anchor tag to the text content, the anchor tag including an entity ID and a clinical attribute both associated with the clinical named entity, thereby generating an enhanced input document; and submit a first query prompt and the enhanced input document to a generative artificial intelligence (GAI) model, the first query prompt including task text and anchoring markup text, the task text includes an instruction of a task to be performed by the GAI model on the enhanced input document, the anchoring markup text includes a template of the anchor tag and an instruction to add a reference anchor tag to an output generated by the GAI model, wherein the reference anchor tag is to include the entity ID and the clinical attribute of the anchor tag.

2. The input augmentation system of claim 1, wherein the instructions are further operative to:

generate the entity ID as a unique identifier for the clinical named entity;

search a clinical ontology for the clinical named entity; and identify the clinical attribute as an entity type of the clinical named entity, the entity type being a parent of the clinical named entity within a hierarchy of the clinical ontology.

3. The input augmentation system of claim 1, wherein the instructions are further operative to determine that the clinical named entity satisfies a clinical criterion based on the clinical attribute of the clinical named entity, wherein adding the anchor tag to the text content is based on the determining.

4. The input augmentation system of claim 1, wherein the instructions are further operative to:

submit at least a portion of the text content to a named entity recognition (NER) model, the NER model being trained on a vocabulary of clinical entities and configured to output names of named entities appearing within input text;

receive, as output from the NER model, the clinical named entity; and identify an occurrence of the clinical named entity within the text content, wherein adding the anchor tag includes adding the anchor tag one of before, after, or around the occurrence of the clinical named entity within the text content.

5. The input augmentation system of claim 1, wherein the instructions are further operative to:

receive output text from the GAI model in response to the submitting;

determine that the output text does not include a reference to the entity ID of the clinical named entity; and submit a second query prompt to the GAI model, the second query prompt instructing the GAI model to update the output text to include a reference to the entity ID.

6. The input augmentation system of claim 1, wherein the instructions are further operative to:

receive output text from the GAI model in response to the submitting, the output text including the reference anchor tag, the reference anchor tag including the entity ID associated with the clinical named entity;

cause the output text to be displayed via a user interface;

receive user input identifying the reference anchor tag;

in response to the user input, search the text content of the enhanced input document for the anchor tag based on the entity ID appearing in the reference anchor tag; and display at least a portion of the text content around the anchor tag.

7. The input augmentation system of claim 1, wherein the instructions are further operative to generate the entity ID and the clinical attribute for the clinical named entity, wherein the anchor tag including the entity ID and the clinical attribute is added surrounding or adjacent to the clinical named entity within the text content of the clinical input document to generate the enhanced input document.

8. A computer-implemented method of augmenting text inputs for analyzing clinical documents, the method comprising:

identifying a clinical named entity within text content of a clinical input document based on output from a named entity recognition (NER) model;

adding an anchor tag to the text content, the anchor tag including an entity ID and a clinical attribute associated with the clinical named entity, thereby generating an enhanced input document; and submitting a first query prompt and the enhanced input document to a language model (LM), the first query prompt including task text and anchoring markup text, the task text includes instructions of a task to be performed by the LM on the enhanced input document, the anchoring markup text includes a template of the anchor tag and instructions to add a reference anchor tag to output generated by the LM, wherein the reference anchor tag is to include the entity ID and the clinical attribute of the anchor tag.

9. The computer-implemented method of claim 8, further comprising:

searching a clinical ontology for the clinical named entity; and identifying the clinical attribute as an entity type of the clinical named entity, the entity type being a parent of the clinical named entity within a hierarchy of the clinical ontology.

10. The computer-implemented method of claim 8, further comprising determining that the clinical named entity satisfies a clinical criterion based on the clinical attribute of the clinical named entity, wherein adding the anchor tag to the text content is based on the determining.

11. The computer-implemented method of claim 8, further comprising:

submitting at least a portion of the text content to the NER model, the NER model being trained on a vocabulary of clinical entities and configured to output names of named entities appearing within input text;

receiving, as output from the NER model, the clinical named entity; and identifying an occurrence of the clinical named entity within the text content, wherein adding the anchor tag includes adding the anchor tag one of before, after, or around the occurrence of the clinical named entity within the text content.

12. The computer-implemented method of claim 8, further comprising:

receiving output text from the LM in response to the submitting;

determining that the output text does not include a reference to the entity ID of the clinical named entity; and submitting a second query prompt to the LM, the second query prompt instructing the LM to update the output text to include a reference to the entity ID.

13. The computer-implemented method of claim 8, further comprising:

receiving output text from the LM in response to the submitting, the output text including the reference anchor tag, the reference anchor tag including the entity ID associated with the clinical named entity;

transmitting the output text to another computing device for display via a user interface;

receiving user input identifying the reference anchor tag;

in response to the user input, searching the text content of the enhanced input document for the anchor tag based on the entity ID appearing in the reference anchor tag; and transmitting at least a portion of the text content around the anchor tag to the other computing device for display via the user interface.

14. The computer-implemented method of claim 8, further comprising causing a query configuration screen to be displayed via a user interface, the query configuration screen including one or more of a filter criteria section, a tag format section, a task selection section, and an input text section, the filter criteria section allowing configuration of a first filter criterion, the tag format section allowing configuration of the template, the task selection section allowing selection of a task, and the input text section allowing input of the text content.

15. A computer storage device having computer-executable instructions stored thereon, which, on execution by a computer, cause the computer to perform operations comprising:

identifying a named entity within text content of an input document;

adding an anchor tag to the text content, the anchor tag including an entity ID and an attribute associated with the named entity, thereby generating an enhanced input document; and submitting a first query prompt and the enhanced input document to a generative artificial intelligence (GAI) model, the first query prompt including task text and anchoring markup text, the task text includes instructions of a task to be performed by the GAI model on the enhanced input document, the anchoring markup text includes a template of the anchor tag and instructions to add a reference anchor tag to output generated by the GAI model, wherein the reference anchor tag is to include the entity ID and the attribute of the anchor tag.

16. The computer storage device of claim 15, the operations further comprising:

searching a clinical ontology for the named entity; and identifying the attribute as an entity type of the named entity, the entity type being a parent of the named entity within a hierarchy of the clinical ontology.

17. The computer storage device of claim 15, the operations further comprising:

submitting at least a portion of the text content to a named entity recognition (NER) model, the NER model being trained on a vocabulary of clinical entities and configured to output names of named entities appearing within input text;

receiving, as output from the NER model, the named entity; and identifying an occurrence of the named entity within the text content, wherein adding the anchor tag includes adding the anchor tag one of before, after, or around the occurrence of the named entity within the text content.

18. The computer storage device of claim 15, the operations further comprising:

receiving output text from the GAI model in response to the submitting;

determining that the output text does not include a reference to the entity ID of the named entity; and submitting a second query prompt to the GAI model, the second query prompt instructing the GAI model to update the output text to include a reference to the entity ID.

19. The computer storage device of claim 15, the operations further comprising:

receiving output text from the GAI model in response to the submitting, the output text including the reference anchor tag, the reference anchor tag including the entity ID associated with the named entity;

transmitting the output text to another computing device for display via a user interface;

receiving user input identifying the reference anchor tag;

in response to the user input, searching the text content of the enhanced input document for the anchor tag based on the entity ID appearing in the reference anchor tag; and transmitting at least a portion of the text content around the anchor tag to the other computing device for display via the user interface.

20. The computer storage device of claim 15, the operations further comprising causing a query configuration screen to be displayed via a user interface, the query configuration screen including one or more of a filter criteria section, a tag format section, a task selection section, and an input text section, the filter criteria section allowing configuration of a first filter criterion, the tag format section allowing configuration of the template, the task selection section allowing selection of a task, and the input text section allowing input of the text content.

* * * * *